United States Patent
Panin et al.

(10) Patent No.: US 12,169,260 B2
(45) Date of Patent: Dec. 17, 2024

(54) MEAN RANDOMS ESTIMATION FROM LIST MODE DATA

(71) Applicant: Siemens Medical Solutions USA, Inc., Malvern, PA (US)

(72) Inventors: Vladimir Panin, Knoxville, TN (US); Mehmet Aykac, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 559 days.

(21) Appl. No.: 17/302,347

(22) Filed: Apr. 30, 2021

(65) Prior Publication Data

US 2022/0350037 A1    Nov. 3, 2022

(51) Int. Cl.

| | |
|---|---|
| *G01T 1/164* | (2006.01) |
| *A61B 6/00* | (2024.01) |
| *G01T 1/29* | (2006.01) |
| *G01T 1/36* | (2006.01) |
| *G06T 11/00* | (2006.01) |

(52) U.S. Cl.
CPC .......... *G01T 1/1642* (2013.01); *A61B 6/5211* (2013.01); *G01T 1/2985* (2013.01); *G01T 1/362* (2013.01); *G06T 11/005* (2013.01); *G06T 2207/10104* (2013.01)

(58) Field of Classification Search
CPC ................. A61B 6/5211; G06T 11/005; G06T 2207/10104
See application file for complete search history.

(56) References Cited

U.S. PATENT DOCUMENTS

| | | | | |
|---|---|---|---|---|
| 8,094,908 | B2* | 1/2012 | Stearns | G01T 1/2985 |
| | | | | 250/363.04 |
| 9,044,153 | B2* | 6/2015 | Panin | G06T 11/005 |
| 10,127,690 | B2* | 11/2018 | Ye | G06T 7/0012 |
| 11,393,138 | B2* | 7/2022 | Song | G06T 7/0012 |

(Continued)

OTHER PUBLICATIONS

Panin, V. Y. et al., "Simultaneous update iterative algorithm for variance reduction on random coincidences in PET", IEEE Nuclear Science Symposium Conference Record, 2007, DOI: 10.1109/NSSMIC.2007.4436722, 5 pages (Year: 2007).*

(Continued)

*Primary Examiner* — Matthew C Bella
*Assistant Examiner* — Janice E. Vaz

(57) ABSTRACT

Systems and methods to estimated mean randoms include acquisition of list mode data describing true coincidences and delay coincidences detected by a positron emission tomography scanner during a scan of an object, determination, for each crystal of the positron emission tomography scanner and for each of a plurality of time periods of the scan, of delay coincidences including the crystal based on the list mode data, determination, each crystal, of determine a singles rate associated with each time period based on the delay coincidences determined for the crystal over the time period, determination, for each time period, of determine estimated mean randoms for each of a plurality of pairs of the crystals based on the singles rate associated with the time period for each crystal of the crystal pair, and reconstruction of an image of the object based on the estimated mean randoms for each time period and the detected true coincidences.

17 Claims, 8 Drawing Sheets

(56) References Cited

U.S. PATENT DOCUMENTS

2017/0345189 A1* 11/2017 Liu ...................... A61B 6/4208
2020/0363542 A1* 11/2020 Song ...................... G01T 1/171

OTHER PUBLICATIONS

Panin, V. Y. et al., "Simultaneous update iterative algorithm for variance reduction on random coincidences in PET", IEEE Nuclear Science Symposium Conference Record, 2007, DOI:10.1109/NSSMIC.2007.4436722, 5 pages.

Panin, V.Y. et al. "TOF Data Non-Rigid Motion Correction", IEEE Xplore, 2015, [Downloaded on Apr. 17, 2024], 5pgs.

Panin, V. Y., et al., "Continuous bed motion on clinical scanner: design, data correction, and reconstruction", Physics in Medicine & Biology, Phys. Med. Biol. 59 (2014), doi:10.1088/0031-9155/59/20/6153, (pp. 6153-6174, 22 total pages.

* cited by examiner

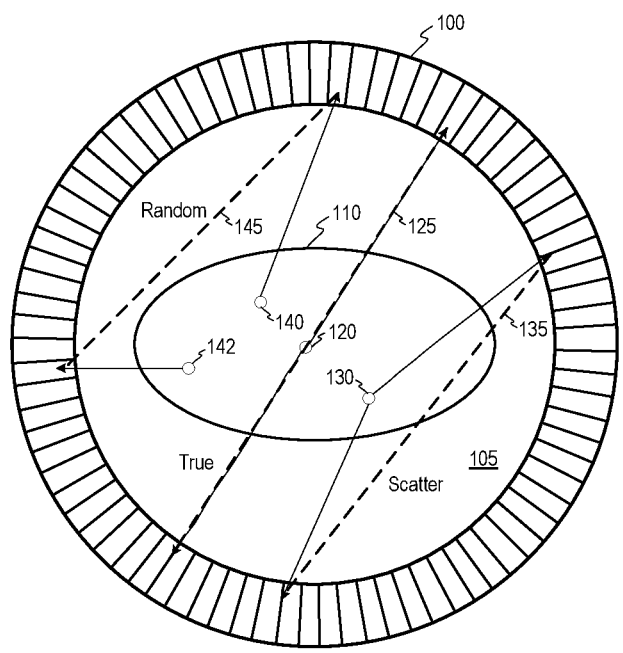 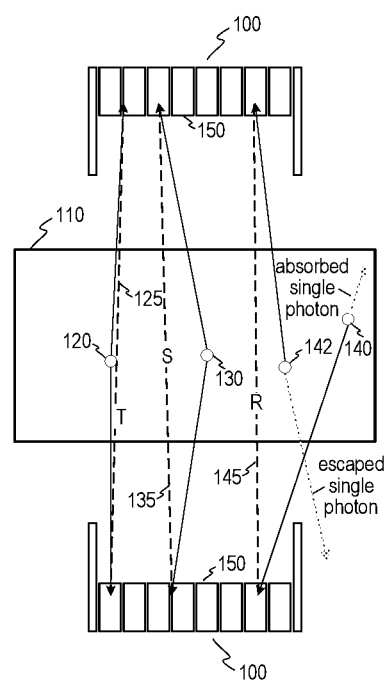
FIG. 1A  FIG. 1B

MEAN RANDOMS ESTIMATION FROM LIST MODE DATA

BACKGROUND

According to conventional positron-emission-tomography (PET) imaging, a radiopharmaceutical tracer is introduced into a patient body, typically via radial arterial injection. Radioactive decay of the tracer generates positrons which eventually encounter electrons and are annihilated thereby. Annihilation produces two photons which travel in approximately opposite directions.

A ring of detectors surrounding the body detects the emitted photons, identifies "coincidences", and reconstructs PET images based on the identified coincidences. A coincidence is identified when two detectors disposed on opposite sides of the body detect the arrival of two photons within a particular coincidence time window. Because the two "coincident" photons travel in approximately opposite directions, the locations of the two detectors determine a Line-of-Response (LOR) along which an annihilation event may have occurred.

A "true" coincidence represents the detection of two coincident photons which arose from a single annihilation event located on a LOR between the two detectors. A "random" coincidence represents two coincident photons which did not arise from the same annihilation event. A "scatter" coincidence is a type of true coincidence in which two coincident photons originated from the same annihilation event but the annihilation event was not located along the LOR of the two detectors because one or both of the photons interacted and scattered within the body or media.

Conventional PET scanners detect all coincidences without regard to whether the coincidences are true, random or scatter coincidences. Since only the true coincidences represent spatial information regarding the distribution of the tracer within the body, random and scatter coincidences should be addressed prior to and/or during image reconstruction. Software and/or hardware-based approaches can be used to estimate random coincidences.

One current approach involves delaying one input channel of detected events. For example, main hardware logic detects all true coincidences along all LORs as described above. Additional "delay logic" receives the same inputs as the main logic but delays one input channel by, for example, a few tens of nanoseconds (e.g., 5× the coincidence window) and then performs coincidence detection. As a result, the delay logic does not detect any actual true coincidences.

The coincidences detected by the delay logic (i.e., the delay coincidences) are currently used to estimate singles rates for each crystal of the PET scanner. The singles rate is the rate at which a crystal detects valid (i.e., energy-qualified) photons during the course of a scan. Next, for each LOR (i.e., each crystal pair (i,j)), mean randoms $\bar{r}_{ij}$ are constructed using the randoms smoothing model: $\bar{r}_{ij}=2\tau s_i s_j$, where $s_i$ and $s_j$ are the singles rate for crystals i and j and $\tau$ is the coincidence time window. Some techniques further apply rescaling to the constructed mean randoms $\bar{r}_{ij}$ based on the delay coincidence counts. In either case, the resulting mean randoms may then be accounted for during reconstruction of a PET image from the detected true coincidences as is known in the art.

The above techniques fail to adequately account for situations in which the singles rate varies in time. These situations include, but are not limited to, Continuous Bed Motion (CBM) scans and stationary scans in which tracer distribution changes rapidly. Moreover, the aforementioned scaling, which is performed plane-by-plane, is noise sensitive. This sensitivity is particularly problematic for oblique segments in CBM acquisition, which are noisy due to their low number of counts and especially prevalent in long axial field-of-view PET scanners.

BRIEF DESCRIPTION OF THE DRAWINGS

FIGS. 1A and 1B illustrate detection of coincidences according to some embodiments.

DETAILED DESCRIPTION

Figure 2:
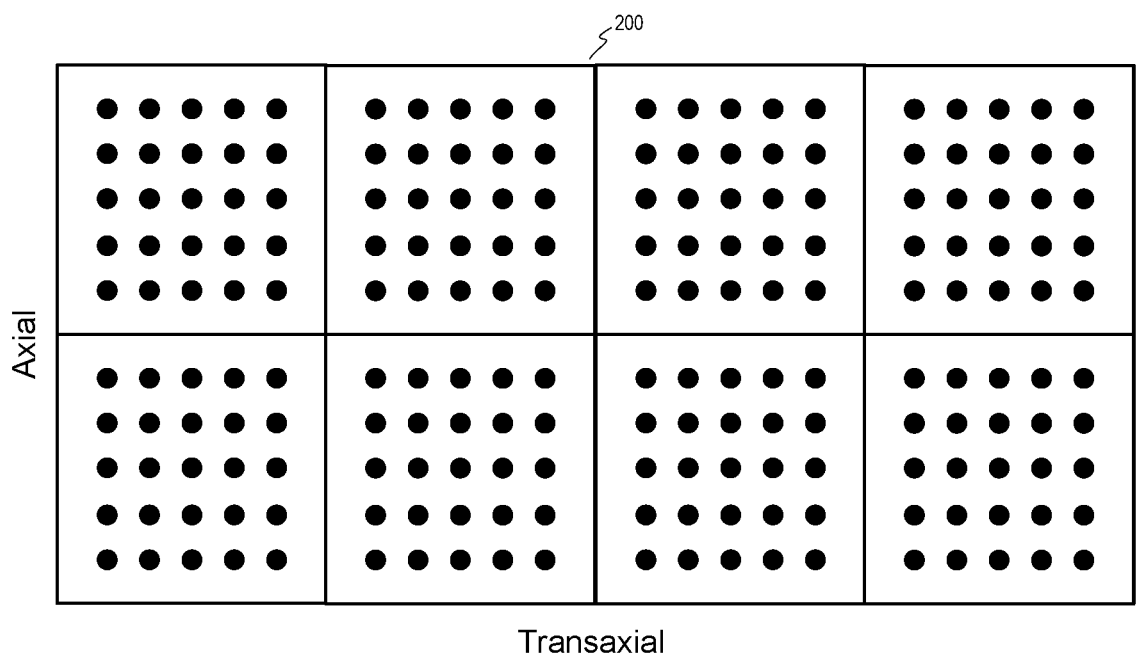
FIG. 2 illustrates a PET detector according to some embodiments.

The following description is provided to enable any person in the art to make and use the described embodiments. Various modifications will remain apparent to those in the art.

The inventors have discovered that randoms smoothing model $\bar{r}_{ij}=\int s_i(t)s_j(t)dt$, provides an improved estimation of mean randoms as compared to prior models. By providing a better estimate of mean randoms, embodiments may provide improved PET images reconstructed based thereon. Such improvements are particularly significant in scenarios where singles rates vary widely in time. The randoms smoothing model can be used without additional heuristic methods, the application of which may lead to data correction errors and therefore to degraded image quality.

Estimation of mean randoms based on the above model requires determination of singles rates of each pair of crystals i, j as functions of time. This determination may be impractical from a processing standpoint, since estimation of singles from a sinogram is unpractical, and direct acquisition of singles per crystal is not available. The inventors have addressed this issue by estimating singles rates over time based on cone-sums representing delay coincidences over time.

Advantageously, the number of cone-sums determined for a given time period (which represent the delay coincidences detected over the time period) is equal to the number of crystals in the PET scanner. In contrast, a delay coincidence sinogram represents the delay coincidences using a number of LORs equal to the square of the number of crystals. The determined cone-sums therefore comprise a highly-compressed representation of the delay coincidences, which is easier to compute and subject to further processing. Moreover, the cone-sums may be determined directly and efficiently from PET scan list mode data.

FIG. 1A and FIG. 1B illustrate detection of coincidences according to some embodiments. FIG. 1A is an axial view of bore 105 of detector ring 100 and imaging object 110 disposed therein. Imaging object 110 may comprise a human body, a phantom, or any other suitable object. FIG. 1B is a transaxial view of detector ring 100 and object 110 of FIG. 1A. Detector ring 100 is composed of an arbitrary number (eight in this example) of adjacent and coaxial rings of detectors 150 in the illustrated example. Each detector 150 may comprise any number of scintillator crystals and electrical transducers.

Annihilation events 120, 130, 140 and 142 are assumed to occur at various locations within object 110. As described above, an injected tracer generates positrons which are annihilated by electrons to produce two 511 keV gamma photons which travel in approximately opposite directions. Each annihilation event represented in FIG. 1A and FIG. 1A results in the detection of a coincidence. As also noted above, true coincidences represent valid image data, while scatter and random coincidences represent noise.

A coincidence is detected when a pair of detectors receive two gamma photons within the coincidence time window, as determined based on the calculated arrival times of the two gamma photons at their respective detectors. Event 120 is associated with a true coincidence because event 120 resulted in two gamma photons which were received within the coincidence time window and because the position of annihilation event 120 lies on LOR 125 connecting the detector positions at which the two gamma photons were received.

Event 130 is associated with a scatter coincidence because, even though the two gamma photons resulting from event 130 were detected within the coincidence time window, the position of annihilation event 130 does not lie on LOR 135 connecting the two photon positions. This may be due to Compton (i.e., inelastic) or Coherent (i.e., elastic) scatter resulting in a change of direction of at least one of the two gamma photons within object 110.

Events 140 and 142 are two separate annihilation events which result in detection of a random coincidence. As shown in FIG. 1B, one of the photons generated by event 140 is absorbed in object 110 and one of the photons generated by event 142 escaped detection by any detector 150 of detector ring 100. The remaining photons happen to be detected within the coincidence time window, even though no annihilation event occurred on LOR 145 connecting the positions at which the coincident photons were received.

Since only the true unscattered coincidences indicate locations of annihilation events, random coincidences and scatter coincidences are often subtracted from or otherwise used to correct acquired PET data during reconstruction of a PET image.

Generally, a PET detector includes one or more scintillation elements and one or more electrical transducers. The scintillation elements create photons with the energy of a few electron volts (eV) in response to receiving the 511 keV photons which result from annihilation events. The electrical transducers convert the low-energy photons created by the scintillation elements to electrical signals. According to some embodiments, the electrical transducers may comprise, for example, SiPMs, PMTs, or semiconductor-based detectors.

FIG. 2 illustrates detector 200 according to some embodiments. Detector 200 consists of eight mini-blocks, with two mini-blocks in the axial direction and four mini-blocks in the transaxial direction. In one example, a mini-block comprises a grid of 5×5 lutetium oxyorthosilicate (LSO) scintillation crystals having dimensions of 3.2 mm×3.2 mm×20 mm. A mini-block may be coupled to a 4×4 array of SiPMs for receiving light photons therefrom and generating electrical signals based thereon. Detector 200 therefore includes 200 crystals, with rows of 10 crystals in the axial direction and 20 crystals in the transaxial direction. Embodiments are not limited to the above description of detector 200.

According to some embodiments, detector ring 100 includes 8 detectors in the axial direction and 38 detectors in the transaxial direction. As such, detector ring 100 includes 60800 detector crystals, with rows of 80 detector crystals in the axial direction and rows of 760 detector crystals in the transaxial direction. Embodiments are not limited to these specifications.

Figure 3:
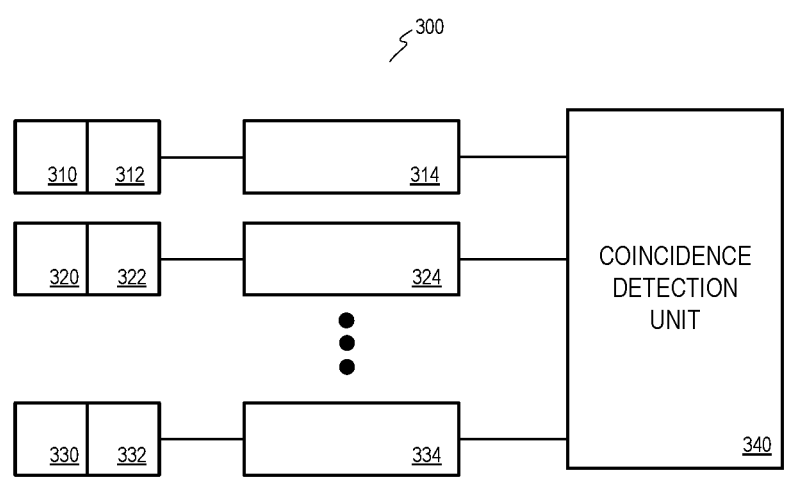
FIG. 3 is a block diagram of a coincidence detection system according to some embodiments.

FIG. 3 is a block diagram of coincidence detection system 300 according to some embodiments. System 300 includes scintillation units 310, 320 and 330, respective electrical transducer units 312, 322 and 332, and respective signal processing components 314, 324 and 334. Coincidence detection unit 340 receives signals from each of signal processing components 314, 324 and 334.

Each of scintillation units 310, 320 and 330 may include one or more scintillation crystals. For example, each of scintillation units 310, 320 and 330 may comprise a mini-block of 5×5 crystal elements, a macro-block of 2×2 mini-blocks, or a detector composed of two macro-blocks. Embodiments are not limited to any particular configuration or construction of scintillation units 310, 320 and 330.

Each of electrical transducer units 312, 322 and 332 may comprise one or more PMTs, SiPMs or the like. The number of electrical transducers in each of units 312, 322 and 332 may be less than, equal to, or greater than the number of crystal elements in each of scintillation units 310, 320 and 330. According to some embodiments, an electrical transducer unit includes one 4×4 array of SiPMs for each mini-block of 5×5 crystal elements in its corresponding scintillation unit.

Signal processing components 314, 324 and 334 receive electrical signals from respective electrical transducer units 312, 322 and 332 and perform signal processing to, for example, determine whether a signal represents a photon detection event, perform signal unpiling by pile-up rejection and/or correction methods, and associate photon detection events with specific detector crystals of scintillation units 310, 320 and 330. Signal processing components 314, 324 and 334 may perform any suitable functions and exhibit any suitable implementations.

Coincidence detection unit 340 receives all photon detection events which pass energy qualification, called singles, and identifies pairs of such events which occurred within a coincidence time window. As described above, coincidence detection unit 340 also includes delay logic which delays the apparent arrival time of one event of each comparison, and thereby identifies the above-described delay coincidences. Coincidence detection unit 340 therefore outputs data specifying each identified pair and denoting each pair as a true coincidence or delay coincidence. For either type of coincidence, the output data also specifies the two detector crystals which received the photon detection events which comprised the coincidence.

Data output by coincidence detection unit 340 and associated with the coincidences detected over a period of time may be stored in a "list mode" file. The list mode file includes list mode data, which specifies, for each coincidence, the type of the coincidence (i.e., true or delay), the two crystals which received the photons of the coincidence, the energy level of each event, the time at which the coincidence was detected and, in the case of time-of-flight (TOF) PET imaging, is the difference between the arrival times of the two photons whose detection resulted in the detected coincidence. This difference may be used to more accurately estimate a particular position along the LOR at which the corresponding annihilation event occurred. The list mode data is not limited to the above.

The coincidences detected over a period of time may also be stored in a sinogram. A sinogram is a data array of the angle versus the displacement of each LOR of each detected coincidence. A delays sinogram may store data relating to the detected delay coincidences while a trues sinogram may store data relating to the detected true coincidences. A sinogram includes one row containing the LOR for a particular azimuthal angle φ. Each of these rows corresponds to a one-dimensional parallel projection of the tracer distribution at a different coordinate. A sinogram stores the location of the LOR of each coincidence such that all the LORs passing through a single point in the volume trace a sinusoid curve in the sinogram. A sinogram may represent each coincidence by its LOR, energy level, the time at which the coincidence occurred, TOF data and other information.

Figure 4:
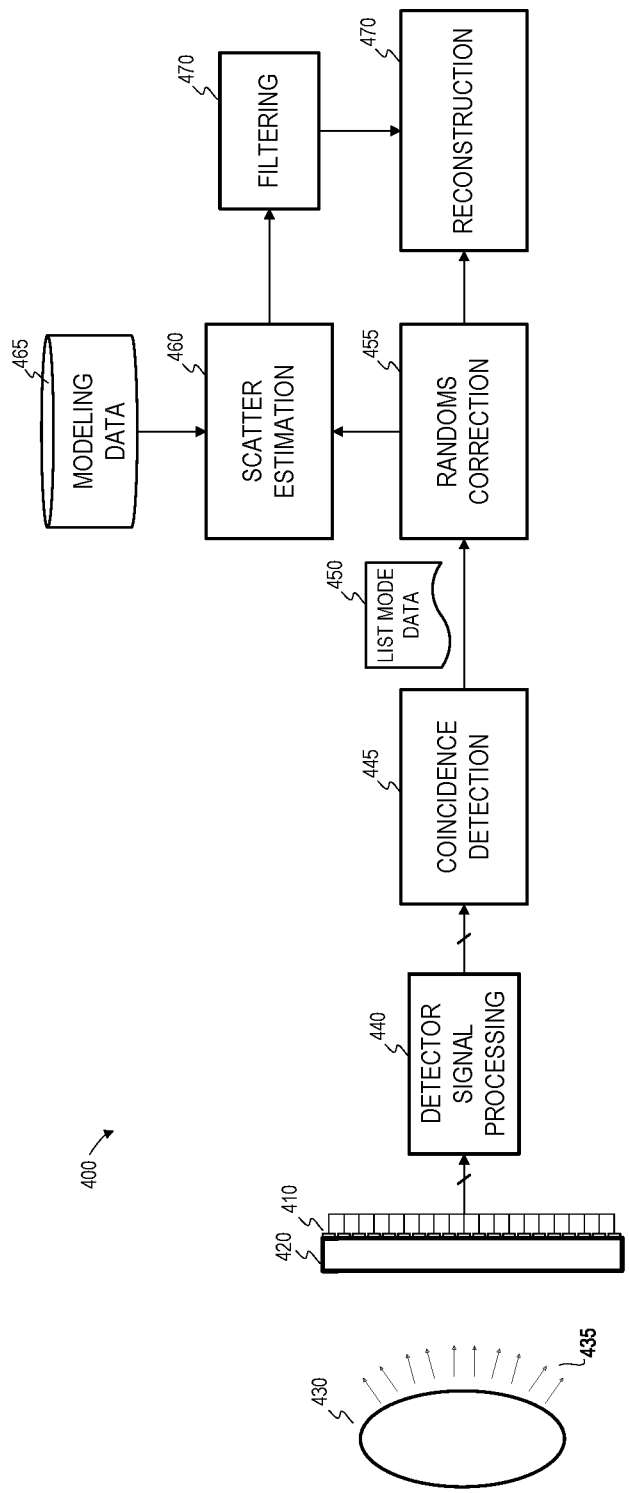
FIG. 4 is a block diagram of a system to reconstruct an image from PET data according to some embodiments.

FIG. 4 illustrates imaging system 400 according to some embodiments. Each component of system 400 may be implemented by any suitable combination of hardware and software. One or more components may be implemented by a single software application in some embodiments.

System 400 includes detectors 410 of a portion of a detector ring and corresponding scintillator 420. Scintillator 420 may be comprised of individual crystals as described with respect to FIG. 2. Embodiments are not limited to scintillator-based detectors. Direct conversion detectors (e.g., CZT and TlBr) may also be used in conjunction with some embodiments.

Detectors 410 detect gamma photons 435 emitted from volume 430. Systems for facilitating the emission of gamma photons from a volume are known in the art, and in particular with respect to the PET imaging described herein. As described above, crystals of scintillator 420 receive the gamma photons 435 and emits light photons in response. Detectors 410 receive the light photons and each detector 410 generates electrical signals based on the energy of the received photons and its own characteristic photoelectric response profile.

Detector signal processing unit 440 receives the electrical signals generated by each detector 410 and performs signal processing to, for example, determine whether a signal represents a photon detection event, perform signal unpiling by pile-up rejection, determine an event energy, and determine an event time. Detector signal processing unit 440 may perform any suitable functions and exhibit any suitable implementations.

During a given time period, coincidence detection unit 445 receives all photon detection events which pass energy qualification (e.g., between 435 and 585 keV) from all detectors 410 of the detector ring. Based on the reception time of each photon detection event, unit 445 identifies pairs of photon detection events which were received within a coincidence time window and determines that each such pair corresponds to a true coincidence having an associated LOR and energy. Coincidence detection unit 445 may also determine, for each pair of photon detection events, a TOF value representing a difference in the reception time of the photon detection events. Coincidence detection unit 445 also uses delay logic to identify delay coincidences as described above. Data representing each detected coincidence (i.e., trues and delays) is stored in file 450.

Randoms correction unit 455 may estimate mean randoms per crystal pair based on file 450 as described herein. The estimation is based on data of file 450 which is associated with detected delay coincidences. Randoms correction unit 455 may correct the true coincidence data of file 450 to generate randoms-corrected (i.e., net trues) data. Scatter estimation unit 460 may then estimate scatter coincidences based on the net trues data according to some embodiments. The estimation may be based in part on modeling data 465 as is known in the art.

The estimated scatter coincidences may be subjected to filtering 470. Reconstruction unit 475 executes a reconstruction algorithm to reconstruct an image based on the thus-filtered estimated scatter coincidences and on the randoms-corrected coincidence data output from randoms correction unit 455.

Figure 5:
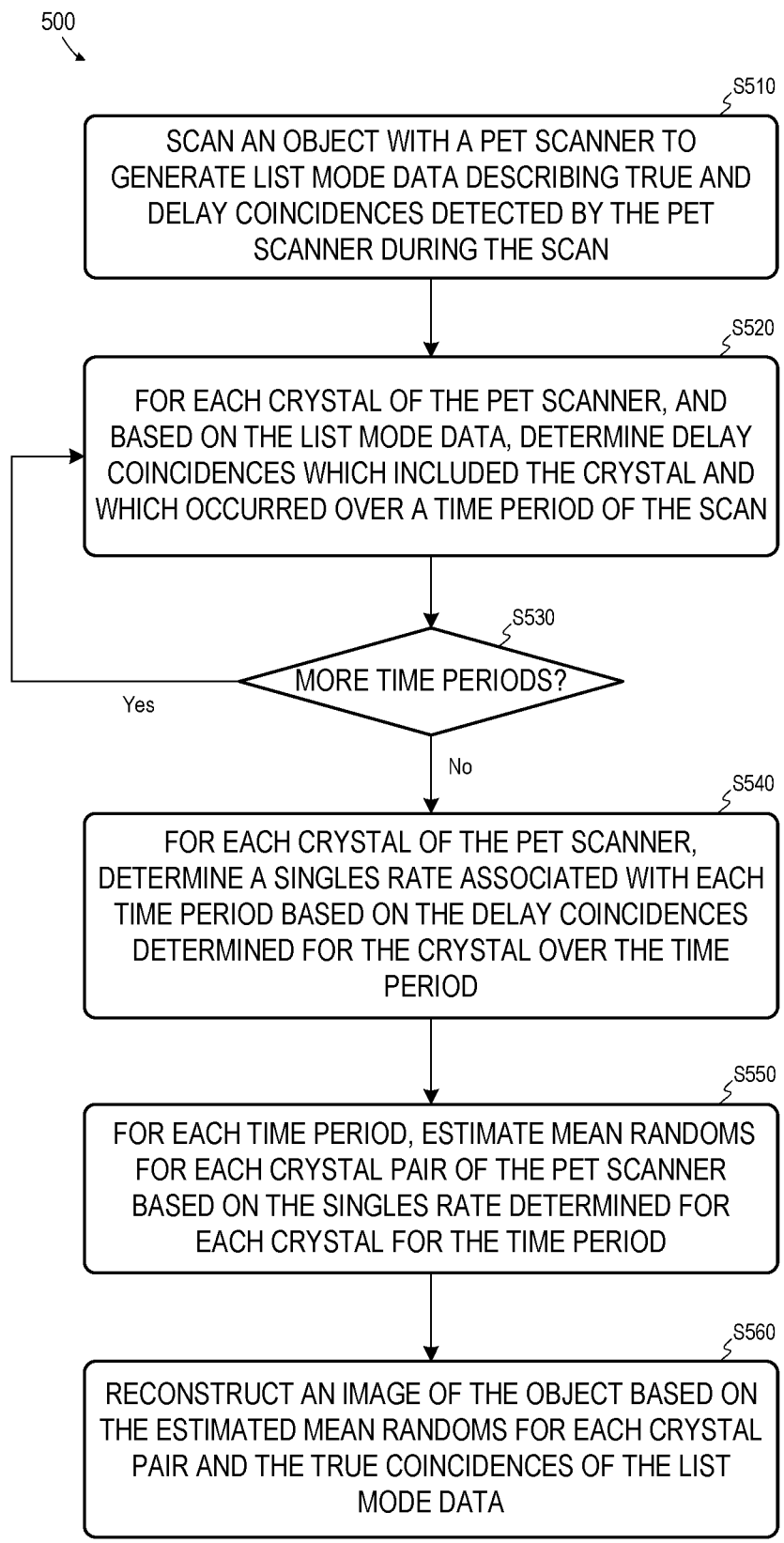
FIG. 5 comprises a flow diagram of a process to estimate mean randoms according to some embodiments.

FIG. 5 comprises a flow diagram of process 500 to estimate mean randoms from list mode data according to some embodiments. The mean randoms may be used to correct the PET frame prior to image reconstruction.

Process 500 and other processes described herein may be executed using any suitable combination of hardware and software. Software program code embodying these processes may be stored by any non-transitory tangible medium, including a fixed disk, a volatile or non-volatile random-access memory, a DVD, a Flash drive, and a magnetic tape, and executed by any suitable processing unit, including but not limited to one or more microprocessors, microcontrollers, processing cores, and processor threads. Embodiments are not limited to the examples described below.

Initially, at S510, an object is scanned using a PET scanner as is known in the art. According to some embodiments, the object comprises a phantom such as, for example, a uniform water-filled cylinder. A radionuclide tracer is injected into the object prior to the scan. The radionuclide tracer may comprise any suitable tracer, such as but not limited to fluorodeoxyglucose (FDG). The scan may comprise a conventional static PET scan or a CBM scan, and generates list mode data describing delay coincidences and true coincidences detected by the PET scanner during the scan as described above.

For each crystal of the PET scanner, a number of delay coincidences which included the crystal and which occurred over a given period of time is determined from the list mode data at S520. S520 comprises determination, for the given time period, of the above-described cone-sum for each crystal of the PET scanner. As described above, the list mode data associates each determined delay coincidence $d_{ij}$ with two crystals i,j of the PET scanner. The number of determined delay coincidences which are associated with each crystal i of the PET scanner may therefore be determined as $\Sigma_j d_{ij}$.

The time period may comprise any sub-period of the overall scan time. In some embodiments using a CBM scan, the duration of the time period is equal to the time required for the bed to move ~5 cm. This duration therefore depends on the speed of bed movement. For purposes of the present description, it will be assumed that the duration of the time period is 1 second and the given time period in a first iteration of S520 is the first second of the PET scan. Therefore, in the present example, S520 includes determining all detected delay coincidences which occurred during the first 1 second of the scan from the list mode data.

Figure 6:
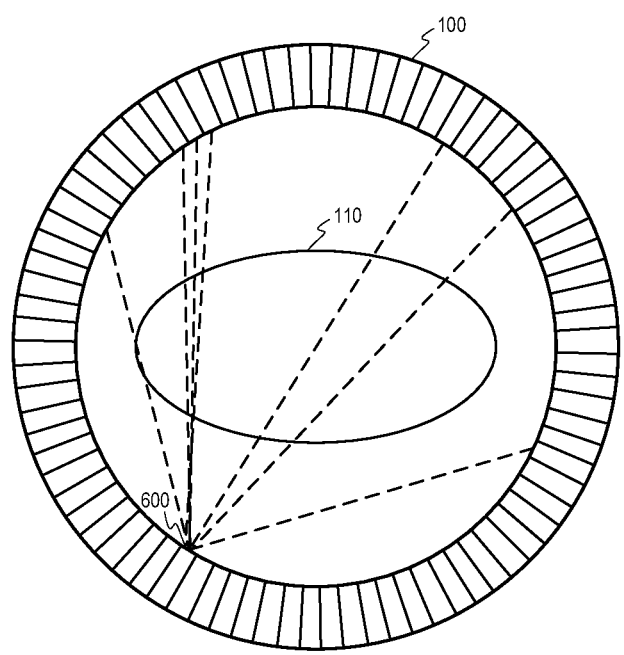
FIG. 6 illustrates determination of a cone-sum for a crystal to some embodiments.

Each dashed line of FIG. 6 represents an LOR of a delay coincidence which occurred during the first 1 second of the scan and which is associated with crystal 600 and another crystal of detector ring 100. It should be understood that many more delay coincidences may have been detected during the first 1 second of the PET scan, and that FIG. 6 illustrates only those delay coincidences which are associated with crystal 600. Accordingly, seven delay coincidences associated with crystal 600 are determined at S520. This determination is repeated for every crystal of the PET scanner.

At S530, it is determined whether the list mode data includes additional time periods. If so, flow returns to S520 to determine delay coincidences per crystal over a next time period. Continuing with the above example, the next time period may comprise the next (i.e., the second) second of the PET scan. Flow continues in this manner to compute a cone-sum for each crystal of the PET scanner for each designated time period of the PET scan.

At S540, and for each time period, a singles rate for each crystal is determined based on the cone-sums determined for each crystal over the time period. In one example, S540 includes iteratively solving the sequential monotonic Coordinate Ascent algorithm $$s_i = \frac{\sum_j d_{ij}}{\sum_j s_j}$$

for each crystal i using the time period-specific cone-sum $\Sigma_j d_{ij}$ determined for each crystal. Alternatively, the singles rate for each crystal i during a time period may be calculated by iteratively solving the following Simultaneous Update equation, again using the time period-specific cone-sum $\Sigma_j d_{ij}$ determined for each crystal and where $N_i$=number of contributing LORs into cone-sum:

$$s_i^{(n+1)} = \frac{-B_i^{(n)} + \sqrt{B_i^{(n)2} + 4N_i C_i}}{2N_i},$$

where $B_i^{(n)} = \sum_j s_j^{(n)} - N_i s_i^{(n)}$, $C_i = \sum_j d_{ij}$, $N = \sum_j$ Next, and for each time period, mean randoms are estimated at S550 for each crystal pair based on the time period-specific singles rates of each crystal. For example, using the singles rates, $s_1$ determined at S540 for crystals i,j for a time period T, the mean randoms $\bar{r}_{ij}$ for the crystal pair (i,j) for the time period T are determined as $\bar{r}_{ij} = 2\tau s_i s_j$.

Figure 7:
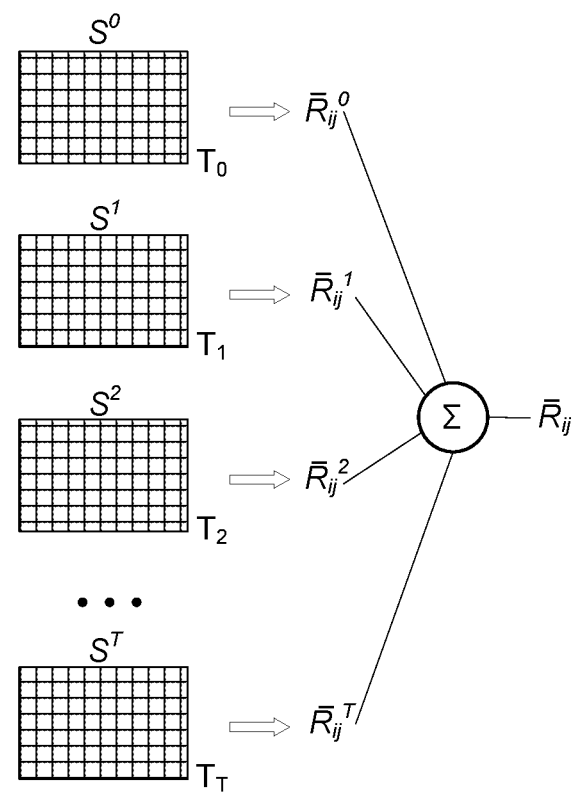
FIG. 7 illustrates estimation of mean randoms based on different acquisition time periods according to some embodiments.

FIG. 7 illustrates the determination of mean randoms $\bar{R}_{ij}^t$ at S550 for each time period $T_t$. Singles rates $S^0$ represent the singles rates of each crystal in the PET scanner during the acquisition time period $T^0$. Using these singles rates, a mean randoms estimate can be determined for each crystal pair (i,j) as $\bar{r}_{ij}^0 = 2\tau s_i^0 s_j^0$. The mean randoms estimates of all crystal pairs of the PET scanner during time period $T^0$ is denoted $\bar{R}_{ij}^0$. Similar determinations occur for each of time periods $T^0$, $T^1$, $T^2$, ..., $T^T$ to determine corresponding mean randoms estimates $\bar{R}_{ij}^0$, $\bar{R}_{ij}^1$, $\bar{R}_{ij}^2$, ..., $\bar{R}_{ij}^T$.

At S560, an image of the object is reconstructed based on the estimated mean randoms for each crystal pair and the true coincidences of the list mode data. According to some embodiments, and as also illustrated in FIG. 7, some embodiments of S560 include summing the time period-specific mean randoms estimates $\bar{R}_{ij}^0$, $\bar{R}_{ij}^1$, $\bar{R}_{ij}^2$, ..., $\bar{R}_{ij}^T$ to generate composite mean randoms estimate $\bar{R}_{ij}$. For example, the mean randoms estimates $\bar{r}_{i_0 j_0}^t$ for crystals $i_0$, $j_0$ over each time period $T^t$ are summed to generate composite mean randoms estimate $\bar{r}_{i_0 j_0}$, and this summation is performed for every crystal pair to generate composite mean randoms estimate $\bar{R}_{ij}$. This summation may comprise an implementation of the above-described randoms smoothing model $\bar{r}_{ij} = \int s_i(t) s_j(t) dt$ (i.e., as $\bar{r}_{ij} = s_i(t) s_j(t)$).

As described with respect to FIG. 4, S560 may include reconstruction, in any manner that is or becomes known, of a PET image based on the detected true coincidences, a scatter estimate, and composite estimated mean randoms $\bar{R}_{ij}$ as described herein. Such a PET image may exhibit less noise and a greater signal-to-noise ratio than an image reconstructed from PET data using prior techniques.

Figure 8:
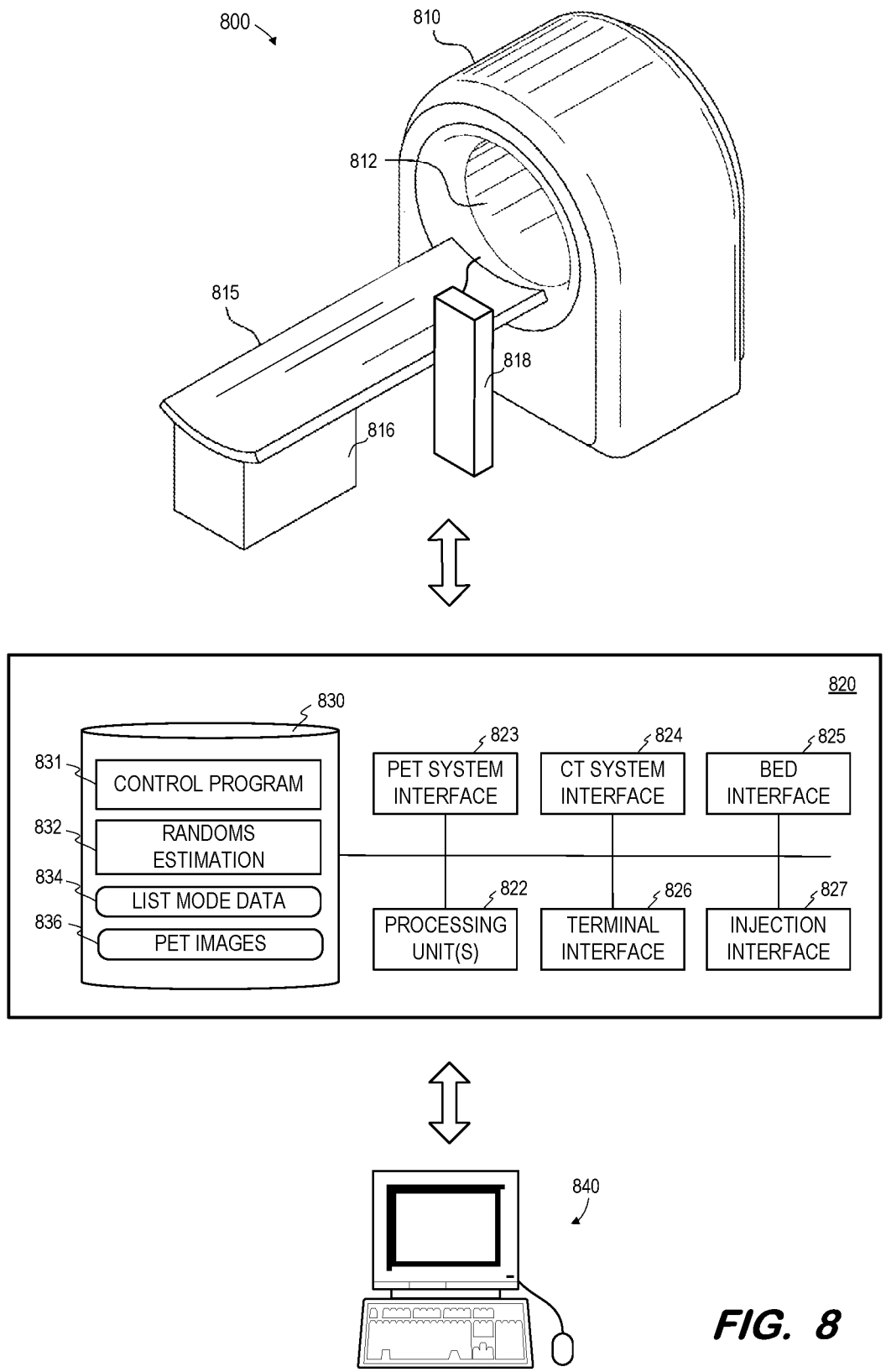
FIG. 8 is a block diagram of a PET/CT imaging system according to some embodiments.

FIG. 8 illustrates PET/CT system 800 to execute one or more of the processes described herein. Embodiments are not limited to system 800.

System 800 includes gantry 810 defining bore 812. As is known in the art, gantry 810 houses PET imaging components for acquiring PET image data and CT imaging components for acquiring CT image data. The CT imaging components may include one or more x-ray tubes and one or more corresponding x-ray detectors as is known in the art.

The PET imaging components may include any number or type of detectors in any configuration as is known in the art. Generally, a detector includes one or more scintillation elements and one or more electrical transducers. The scintillation elements create photons with the energy of few electron volts in response to receiving the 511 keV photons which result from annihilation events. LSO and lutetium yttrium oxyorthosilicate (LYSO) scintillators exhibit suitable stopping power and fast scintillation decay, and may be used in high count rate scenarios.

The electrical transducers convert the low-energy photons created by the scintillation elements to electrical signals. According to some embodiments, the electrical transducers may comprise silicon photo-multipliers (SiPM) or photo-multiplier tubes (PMT)). Some embodiments employ a block detector which includes more scintillation elements than electrical transducers. In a block detector, multiple electrical transducers receive spread-out low-energy photons resulting from absorption of one of the 511 keV annihilation-generated photons. The relative outputs of the transducers are compared in order to determine the absorption location, which in turn identifies the scintillation element, or crystal, which is determined to have received the annihilation photon.

Injection system 818 may operate to deliver calibrated injections of FDG, iodine, or other radiopharmaceuticals to a patient before and/or during a PET scan. In some embodiments, injection system 818 is incorporated into gantry 810. Injection system 818 may support a wired or wireless communications link with control system 820 for receiving information specifying dosage, injection protocol and scan delay.

Bed 815 and base 816 are operable to move a patient lying on bed 815 into and out of bore 812 before, during and after imaging. In some embodiments, bed 815 is configured to translate over base 816 and, in other embodiments, base 816 is movable along with or alternatively from bed 815.

Movement of a patient into and out of bore 812 may allow scanning of the patient using the CT imaging elements and the PET imaging elements of gantry 810. Such scanning may proceed based on scanning parameters such as scan ranges and corresponding scanning speeds. Bed 815 and base 816 may provide continuous bed motion and/or step-and-shoot motion during such scanning according to some embodiments.

Control system 820 may comprise any general-purpose or dedicated computing system. Accordingly, control system 820 includes one or more processing units 822 configured to execute processor-executable program code to cause system 820 to operate as described herein, and storage device 830 for storing the program code. Storage device 830 may comprise one or more fixed disks, solid-state random-access memory, and/or removable media (e.g., a thumb drive) mounted in a corresponding interface (e.g., a USB port).

Storage device 830 stores program code of control program 831. One or more processing units 822 may execute control program 831 to, in conjunction with PET system interface 823, bed interface 825, and injection interface 827, control hardware elements to inject a radiopharmaceutical into a patient, move the patient into bore 812 past PET detectors of gantry 810, and detect coincidence events occurring within the patient. The detected events may be stored in memory 830 as list mode data 834.

One or more processing units 822 may also execute control program 831 to, in conjunction with CT system interface 824, cause a radiation source within gantry 810 to emit radiation toward a body within bore 812 from different projection angles, and to control a corresponding detector to acquire two-dimensional CT data. The CT data may be acquired substantially contemporaneously with the PET data as described above, and may be used for attenuation correction of contemporaneously-acquired list mode data 834 as is known in the art. In this regard, control program 831 may also be executed to reconstruct list mode data 834 of a PET scan into PET images 836 using any reconstruction algorithm that is or becomes known.

Storage device 830 also includes randoms estimation program 832 for estimating mean randoms for use in reconstruction according to some embodiments. As mentioned above and described in detail below, such estimation utilizes singles rates of different scanning time periods which are in turn determined based on time period- and crystal-specific cone-sums of delay coincidences.

PET images 836 may be transmitted via terminal interface 826 to terminal 840 for display. Terminal 840 may comprise a display device and an input device coupled to system 820. Terminal 840 may receive user input for controlling display of the data, operation of system 800, and/or the processing described herein. In some embodiments, terminal 840 is a separate computing device such as, but not limited to, a desktop computer, a laptop computer, a tablet computer, and a smartphone.

Each component of system 800 may include other elements which are necessary for the operation thereof, as well as additional elements for providing functions other than those described herein. Each functional component described herein may be implemented in computer hardware, in program code and/or in one or more computing systems executing such program code as is known in the art. Such a computing system may include one or more processing units which execute processor-executable program code stored in a memory system.

Those in the art will appreciate that various adaptations and modifications of the above-described embodiments can be configured without departing from the claims. Therefore, it is to be understood that the claims may be practiced other than as specifically described herein.

What is claimed is:

1. A system comprising:
a positron emission tomography scanner comprising a plurality of crystals, the positron emission tomography scanner to perform a scan of an object and generate list mode data describing true coincidences and delay coincidences detected by the positron emission tomography scanner during the scan;
a processing unit to:
for each crystal, determine, from the list mode data, a number of delay coincidences which include the crystal for each of a plurality of time periods of the scan;
for each crystal, determine a singles rate associated with each time period based on the number of delay coincidences determined for all of the plurality of crystals for the time period;
for each time period, determine estimated mean randoms for each of a plurality of pairs of the crystals based on the singles rate associated with the time period for each crystal of the crystal pair, where estimated mean randoms determined for a pair of the crystals for a first time period are different from estimated mean randoms determined for the pair of the crystals for a second time period;
for each of the plurality of pairs of crystals, determine a composite estimated mean randoms based on the estimated mean randoms determined for the crystal pair for each time period; and
reconstruct an image of the object based on the composite estimated mean randoms for each of the plurality of pairs of crystals and the detected true coincidences; and
a bed to support the object and to move during the scan, wherein a duration of each of the plurality of the time periods depends on a speed of bed movement during the scan.

2. A system according to claim 1, wherein determination of a singles rate associated with a time period for a crystal comprises determination of $$s_i = \frac{\sum_j d_{ij}}{\sum_j s_j}$$

for each crystal i, where $\sum_j d_{ij}$ is equal to the delay coincidences determined for the crystal i over the time period.

3. A system according to claim 1, wherein determination of a singles rate associated with a time period for a crystal comprises determination of $$s_i^{(n+1)} = \frac{-B_i^{(n)} + \sqrt{B_i^{(n)2} + 4N_i C_i}}{2N_i},$$

for each crystal i where $B_i^{(n)} = \sum_j s_j^{(n)} - N_i s_i^{(n)}$, $C_i = \sum_j d_{ij}$, and $\sum_j d_{ij}$ is equal to the delay coincidences determined for the crystal i over the time period.

4. A system according to claim 1,
the positron emission tomography scanner to perform a second scan of a second object and generate second list mode data describing second true coincidences and second delay coincidences detected by the positron emission tomography scanner during the second scan, and
the processing unit to:
for each crystal, determine, from the second list mode data, a second number of second delay coincidences which include the crystal for each of a second plurality of time periods of the second scan;
for each crystal, determine a second singles rate associated with each second time period based on the second number of second delay coincidences determined for all of the plurality of crystals for the second time period;

for each second time period, determine second estimated mean randoms for each of a plurality of pairs of the crystals based on the second singles rate associated with the second time period for each crystal of the crystal pair, where second estimated mean randoms determined for the pair of the crystals for a second time period is different from second estimated mean randoms determined for the pair of the crystals for another second time period;

for each of the plurality of pairs of crystals, determine a second composite estimated mean randoms based on the second estimated mean randoms determined for the crystal pair for each second time period; and reconstruct an image of the second object based on the second composite estimated mean randoms for each of the plurality of pairs of crystals and the detected second true coincidences.

5. A method comprising:

acquiring list mode data describing true coincidences and delay coincidences detected by a positron emission tomography scanner during a scan of an object;

moving a bed supporting the object during the scan; and for each crystal of the positron emission tomography scanner, determine, from the list mode data, a number of delay coincidences which include the crystal for each of a plurality of time periods of the scan;

for each crystal, determining a singles rate associated with each time period based on the number of delay coincidences determined for all of the plurality of crystals for the time period;

for each time period, determining estimated mean randoms for each of a plurality of pairs of the crystals based on the singles rate associated with the time period for each crystal of the crystal pair, where estimated mean randoms determined for a pair of the crystals for a first time period are different from estimated mean randoms determined for the pair of the crystals for a second time period;

for each of the plurality of pairs of crystals, determining a composite estimated mean randoms based on the estimated mean randoms determined for the crystal pair for each time period; and reconstructing an image of the object based on the composite estimated mean randoms for each of the plurality of pairs of crystals and the detected true coincidences, wherein a duration of each of the plurality of the time periods depends on a speed of bed movement during the scan.

6. A method according to claim 5, wherein determining a singles rate associated with a time period for a crystal comprises determination of $$s_i = \frac{\sum_j d_{ij}}{\sum_j s_j}$$

for each crystal i, where $\Sigma_j d_{ij}$ is equal to the delay coincidences determined for the crystal i over the time period.

7. A method according to claim 5, wherein determining a singles rate associated with a time period for a crystal comprises determination of $$s_i^{(n+1)} = \frac{-B_i^{(n)} + \sqrt{B_i^{(n)2} + 4N_i C_i}}{2N_i},$$

for each crystal i where $B_i^{(n)} = \Sigma_j s_j^{(n)} - N_i s_i^{(n)}$, $C_i = \Sigma_j d_{ij}$, and $\Sigma_j d_{ij}$ is equal to the delay coincidences determined for the crystal i over the time period.

8. A method according to claim 5, further comprising:

acquiring second list mode data describing second true coincidences and second delay coincidences detected by the positron emission tomography scanner during a second scan of a second object;

for each crystal, determining, from the second list mode data, a second number of second delay coincidences which include the crystal for each of a second plurality of time periods of the second scan;

for each crystal, determining a second singles rate associated with each second time period based on the second number of second delay coincidences determined for all of the plurality of crystals for the second time period;

for each second time period, determining second estimated mean randoms for each of a plurality of pairs of the crystals based on the second singles rate associated with the second time period for each crystal of the crystal pair, where second estimated mean randoms determined for the pair of the crystals for a second time period is different from second estimated mean randoms determined for the pair of the crystals for another second time period;

for each of the plurality of pairs of crystals, determining a second composite estimated mean randoms based on the second estimated mean randoms determined for the crystal pair for each second time period; and reconstructing an image of the second object based on the second composite estimated mean randoms for each of the plurality of pairs of crystals and the detected second true coincidences.

9. A non-transitory computer-readable medium storing processor-executable process steps which when executed by a processing unit of a computing system, cause the computing system to:

acquire list mode data describing true coincidences and delay coincidences detected by a positron emission tomography scanner during a scan of an object;

move a bed so supporting the object during the scan; and for each crystal of the positron emission tomography scanner, determine, from the list mode data, delay coincidences which include the crystal for each of a plurality of time periods of the scan;

for each crystal, determine a singles rate associated with each time period based on the number of delay coincidences determined for all of the plurality of crystals for the time period;

for each time period, determine estimated mean randoms for each of a plurality of pairs of the crystals based on the singles rate associated with the time period for each crystal of the crystal pair, where estimated mean randoms determined for a pair of the crystals for a first time period are different from estimated mean randoms determined for the pair of the crystals for a second time period;

for each of the plurality of pairs of crystals, determine a composite estimated mean randoms based on the estimated mean randoms determined for the crystal pair for each time period; and reconstruct an image of the object based on the composite estimated mean randoms for each of the plurality of pairs of crystals and the detected true coincidences, wherein a duration of each of the plurality of the time periods depends on a speed of bed movement during the scan.

10. A medium according to claim 9, wherein determination of a singles rate associated with a time period for a crystal comprises determination of $$s_i = \frac{\sum_j d_{ij}}{\sum_j s_j}$$

for each crystal i, where $\Sigma_j d_{ij}$ is equal to the delay coincidences determined for the crystal i over the time period.

11. A medium according to claim 9, wherein determination of a singles rate associated with a time period for a crystal comprises determination of $$s_i^{(n+1)} = \frac{-B_i^{(n)} + \sqrt{B_i^{(n)2} + 4N_i C_i}}{2N_i},$$

for each crystal i where $B_i^{(n)} = \Sigma_j s_j^{(n)} - N_i s_i^{(n)}$, $C_i = \Sigma_j d_{ij}$, and $\Sigma_j d_{ij}$ is equal to the delay coincidences determined for the crystal i over the time period.

12. A medium according to claim 9, the processor-executable process steps which when executed by a processing unit of a computing system, further cause the computing system to:
acquire second list mode data describing second true coincidences and second delay coincidences detected by the positron emission tomography scanner during a second scan of a second object;
for each crystal, determine, from the second list mode data a second number of second delay coincidences which include the crystal for each of a plurality of second time periods of the second scan based on;
for each crystal, determine a second singles rate associated with each second time period based on the second number of second delay coincidences determined for all of the plurality of crystals for the second time period;
for each second time period, determine second estimated mean randoms for each of a plurality of pairs of the crystals based on the second singles rate associated with the second time period for each crystal of the crystal pair, where second estimated mean randoms determined for the pair of the crystals for a second time period is different from second estimated mean randoms determined for the pair of the crystals for another second time period;
for each of the plurality of pairs of crystals, determining a second composite estimated mean randoms based on the second estimated mean randoms determined for the crystal pair for each second time period; and
reconstruct an image of the second object based on the second composite estimated mean randoms for each of the plurality of pairs of crystals and the detected second true coincidences
wherein a duration of each of the plurality of the time periods depends on a speed of bed movement during the scan.

13. A system according to claim 1, wherein the duration is based on a time required for the bed to move approximately 5 cm during the scan.

14. A system according to claim 1, wherein the duration is 1 second.

15. A method according to claim 5, wherein the duration is based on a time required for the bed to move approximately 5 cm during the scan.

16. A method according to claim 5, wherein the duration is 1 second.

17. A non-transitory computer-readable medium according to claim 9, wherein the duration is based on a time required for the bed to move approximately 5 cm during the scan.

* * * * *